United States Patent [19]
Bungard et al.

[11] Patent Number: 6,045,781
[45] Date of Patent: Apr. 4, 2000

[54] TRANSPARENT SUNSCREEN GELS

[75] Inventors: Andrea Bungard, Essen; Klaus Jenni, Witten; Holger Leidreiter, Hattingen; Alfred Walter, Essen, all of Germany

[73] Assignee: Th. Goldschmidt AG, Essen, Germany

[21] Appl. No.: 09/320,865

[22] Filed: May 27, 1999

[30] Foreign Application Priority Data

May 30, 1998 [DE] Germany .............. 198 24 418

[51] Int. Cl.[7] .............. A61K 7/42; A61K 7/00; A61K 31/74
[52] U.S. Cl. ............ 424/59; 424/60; 424/78.02; 424/78.08; 424/400; 424/401
[58] Field of Search ............ 424/59, 60, 78.02, 424/78.03, 400, 401

[56] References Cited

FOREIGN PATENT DOCUMENTS

| 0 176 884 B1 | 4/1986 | European Pat. Off. . |
| 0 568 102 A1 | 11/1993 | European Pat. Off. . |
| 0 819 426 A2 | 1/1998 | European Pat. Off. . |

*Primary Examiner*—Shelley A. Dodson
*Attorney, Agent, or Firm*—Frommer Lawrence & Haug LLP

[57] ABSTRACT

The invention relates to transparent sunscreen gels comprising (a) silicone oil (b) polyoxyalkylene-organpolysiloxanes of the general formula (I)

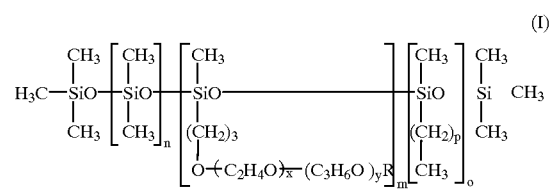

where
R is an alkyl radical or a hydrogen radical,
$n=10$ to 200,
$m=1$ to 25 and
$o=1$ to 100 with the proviso that, in the average molecule, $o \geq m$ and $3o < n$,
$p=7$ to 17, and
the molar mass of the residue $(C_2H_4O-)_x-(C_3H_6O-)_yR$ is from about 250 to about 2000, where x and y are chosen such that the weight ratio of oxyethylene groups to oxypropylene groups is from 100:0 to about 20:80, (c) water, (d) a component chosen from alcohols and/or polyols and (e) at least one UV absorber soluble in the aqueous or in the oily phase.

18 Claims, No Drawings

TRANSPARENT SUNSCREEN GELS

RELATED APPLICATIONS

This application claims priority to German application No. 198 24 418.5, filed May 30, 1998, herein incorporated by reference.

BACKGROUND OF THE INVENTION

1. Field of the Invention

The invention relates to transparent sunscreen gels comprising silicone oil, polyoxyalkylene-organopolysiloxanes, water, a component chosen from alcohols and/or polyols and at least one UV absorber soluble in the aqueous or the oily phase.

2. Description of the Related Art

Transparent emulsions comprising polyol and water/silicone are known and are used, for example, as antiperspirants or hair gels. Matching the refractive index of the aqueous phase to that of the oil phase using polyols, such as glycerol, polyglycerol, propylene glycol, hexane glycol and other polyols, gives transparent emulsions, also called gels. These products are usually prepared using silicone emulsifiers, in which case the oil phase comprises mainly cyclomethicones (cyclic polydimethylsiloxanes) or low molecular weight silicone oils (linear polydimethylsiloxanes).

EP 0 176 884 B1, which corresponds to U.S. Pat. No. 4,698,178 and is herein incorporated by reference, describes the use of polyoxyalkylene-siloxane copolymers containing long-chain alkyl radicals bonded to silicon atoms as emulsifiers for the preparation of W/O emulsions. In particular, this patent specification relates to the use of copolymers of average formula (I)

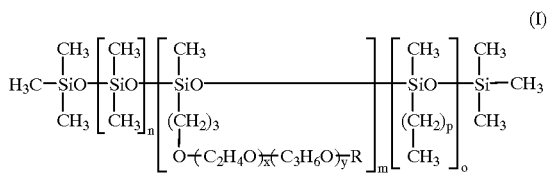

where
R is an alkyl radical having from 1 to 4 carbon atoms or a hydrogen radical,
n=10 to 200,
m=1 to 25 and
o=1 to 100 with the proviso that, in the average molecule,
o≧m and 3o<n,
p=7 to 17, and
the molar mass of the residue $(C_2H_4O—)_x—(C_3H_6O—)_yR$ is from 250 to 2000, where x and y are chosen such that the weight ratio of oxyethylene groups to oxypropylene groups is from 100:0 to 20:80,
as emulsifiers for the preparation of W/O emulsions, the oily phase of which consists of silicone oil or comprises it, in amounts of from 0.3 to 5% by weight, based on the total weight of the emulsion.

Similar α,ω-polyether-polysiloxanes are known as W/O emulsifiers from EP 0 819 426 A2, herein incorporated by reference. This patent application relates to the use of copolymers of the formula (II)

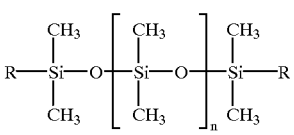

where
$R=—(CH_2—)_mO—(C_2H_4O—)x(C_3H_6O—)_yR^1$
m=2 to 4,
x=3 to 100,
y=0 to 50
$R^1$=H, $CH_3$,$CH_2CH_3$,
n=50 to 200,
as emulsifier in W/O emulsions in amounts of from 0.1 to 20% by weight, based on the total weight of the emulsion.

Furthermore, EP 0 568 102 A1, herein incorporated by reference, discloses silicone gel compositions which comprise
(a) a silicone oil,
(b) a polyoxyalkylene-organopolysiloxane of the general formula (III)

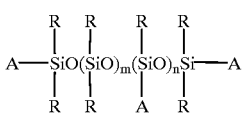

where
R is a methyl or phenyl group,
A is chosen from the group consisting of methyl, phenyl or poloxyalkylene groups of the formula $—C_3H_6O(C_2H_4O)_a(C_3H_6O)_bR'$, where R' is chosen from the group consisting of hydrogen, an acyl group or an alkyl group having from 1 to 4 carbon atoms,
a is an integer in the range from 5 to 50
b is an integer in the range from 5 to 50,
m is an integer in the range from 50 to 1000 and
n is an integer in the range from 1 to 40, and
(c) water.

Conventional sunscreen gels, also called balms, are opaque, emulsion-like hydrogels based on polyacrylates or on hydrocolloids, such as cellulose derivatives or xanthan gum, in most cases in combination with polyacrylates, whose alkyl-modified derivatives have a certain emulsifying action.

Example 1 of EP 0 568 102 A1 describes a sunscreen gel which comprises a silicone oil, an organopolysiloxane, water and one part by weight of a UV absorber Escalol®507. The gel is a water-insoluble, oil-soluble sunscreen filter, namely octyldimethyl PABA. The extremely small amount of sunscreen filter effects only a low sunscreen action. The product Piz Buin Classic Brown Hydro Gel, available commercially from Johnson & Johnson, has the following composition: water, cyclomethicone (and) dimethicone copolyol, glycerol, alcohol, propylene glycol, phenylbenzimidazolsulfonic acid (water-soluble filter), tetrahydroxypropylethylenediamine benzophenone-4 (water-soluble UV filter), fragrances and aroma substances, hyaluronic acid, sodium hydroxide, C.I. 15510, C.I. 47005 (yellow-brown color).

This product corresponds to a transparent W/Si emulsion. The consistency is viscous. The emulsion, referred to as hydrogel, is available in brown squeezable tubes. No cosmetic oils (ester oils, triglycerides) are present and only water-soluble filters are used. The emulsifier "cyclomethicone (and) dimethicone copolyol", which corresponds to the competitor product DC 3225 C from Dow Corning, is unable to stabilize the abovementioned oils or oil-soluble filters. This example has a sun protection factor of 8 in accordance with DIN.

However, if the amount of sunscreen filter is increased, a major change in the refractive index takes place. This means that the gel looses the desired transparency.

OBJECT OF THE INVENTION

Accordingly, the object of the present invention is to provide transparent sunscreen gels which have a high sunscreen action. Moreover, the novel sunscreen gels should be free from polyacrylates.

SUMMARY OF THE INVENTION

Accordingly, it has been found that the above object can be achieved with transparent sunscreen gels comprising silicone oil, polyoxyalkylene-organopolysiloxanes, water, a component chosen from alcohols and/or polyols and at least one UV absorber soluble in the aqueous or in the oily phase.

DESCRIPTION OF THE PREFERRED EMBODIMENTS

Accordingly, the present invention relates, in the first embodiment, to transparent sunscreen gels comprising
(a) silicone oil
(b) polyoxyalkylene-organopolysiloxanes of the formula (I)

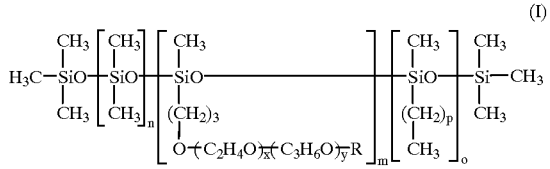

where
R is an alkyl radical, preferably having from 1 to 4 carbon atoms, or a hydrogen radical,
$n=10$ to $200$,
$m=1$ to $25$ and
$o=1$ to $100$ with the proviso that, in the average molecule, $o \geq m$ and $3o < n$,
$p=7$ to $17$, and
the molar mass of the residue $(C_2H_4O\text{—})_x\text{—}(C_3H_6O\text{—})_yR$ is from about 250 to about 2000, where x and y are chosen such that the weight ratio of oxyethylene groups to oxypropylene groups is from 100:0 to about 20:80,
(c) water,
(d) a component chosen from alcohols and/or polyols and
(e) at least one UV absorber soluble in the aqueous or in the oily phase.

Surprisingly, the resulting sunscreen emulsions which, because of their transparent appearance and the solid consistency at room temperature, are referred to as gels. These emulsions have a number of surprising properties.

The novel gels are a new form of sunscreen product. This is the first time that completely transparent sunscreen formulations having sun protection factors of from 9 to 20, determined in accordance with Colipa ("Method of determining the sun protection factor", IKW Brochure, 1st edition, July 1995) and pasty, gel-like consistency have been available. The novel gels can be packaged in any desired container. Particularly suitable forms of packaging are tubes or roll-on dispensers. The refractive index is adjusted here in a manner known per se. As a consequence of a high concentration of sunscreen filters in the oily phase, the novel gels exhibit interesting color phenomena upon interaction with light, which vary depending on the formulation composition and viewing angles. Surprisingly, it has been found that the emulsions, the oily phase of which consists largely of silicone oils and oil-soluble UV filters, have long-term and temperature stability since, in sunscreen emulsions, cosmetic oils are usually used to solubilize the filters. For in-vivo and in-vitro sun protection factor determinations of novel gels which comprise water-soluble UV absorbers, surprisingly high values were measured, which are greater than those of conventional W/O and O/W emulsions.

In contrast to the conventional sunscreen gels, which are opaque hydrogels or emulsifier-free balm formulations, the novel gels are true emulsions having a disperse polyol/aqueous phase. The advantage of the alcohol/polyol+W/Si+oil emulsion structure is that the synergistic effect of water-soluble and oil-soluble filters can be utilized. Furthermore, it is possible to also incorporate cosmetic oils into the novel transparent gels provided the refractive index of the formulation can be adjusted using alcohols/polyols. In this connection, the refractive index of the oils used should be as low as possible. The amount of oils is preferably from about 0.5 to about 5% by weight, based on the overall composition.

In contrast to conventional hydrogels, the novel transparent emulsions are, as a consequence of the emulsion form with coherent oil phase and use of silicone emulsifiers, water-resistant. The addition of liquid organopolysiloxanes to external phases permits a further improvement of the adhesion of the filter substances to the skin and thus is an improvement over existing balms or hydrogels. Non-sticky gels are also obtainable.

For the purposes of the present invention, the silicone oils which are particularly preferred are low to high-viscosity diorganopolysiloxanes, such as dimethylpolysiloxanes, methylphenylpolysiloxanes and dimethylsiloxane-methylphenylsiloxane copolymers; cyclic siloxanes, such as octamethylcyclotetracyclosiloxane, decamethylcyclopentasiloxane and tetramethyltetraphenyltetracyclosiloxane; solutions of cyclic siloxanes of high molar mass; solutions dimethylpolysiloxane gums, dimethylsiloxane-methylphenylsiloxane copolymer gums and dimethylpolysiloxane gums; trimethylsiloxysilicatic acids and cyclic siloxane solutions of trimethylsiloxysilicic acids; diorganopolysiloxanes having $C_6$ to $C_{50}$ alkyl groups; and diorganopolysiloxanes containing amino groups. The silicone oils can be present in the novel gels alone or in combination of two or more components. In particular, preference is given to polysiloxane-polyalkylene copolymers and dialkoxydimethylpolysiloxane.

The content of the silicone oil in the novel gels is not subject to particular restrictions, although silicone oil is preferably used in an amount of from about 10 to about 80% by weight, based on the overall composition.

The polyoxyalkylene-organopolysiloxanes of the general formula (I) serve as emulsifier. The amount of polyoxyalkylene groups in component (b) is not particularly limited, although a preferred content of polyoxyalkylene groups is in the range from about 20 to about 70% by weight. In other respects, component (b) is described in EP 0 818 426 A2 discussed above. It is, of course, also possible to use mixtures of polyoxyalkylene-organosiloxanes.

The component (b) is not subject to any particular restrictions either with regard to the molecular weight or with regard to the viscosity at 25° C. Particularly not when they lead to stable gels which impart a dry feel to the skin.

For the purposes of the present invention, the content of component (b) in the novel gels should preferably be in the range from about 2 to about 30% by weight, particularly preferably in the range from about 5 to about 15% by weight, based on the overall composition. If the content of component (b) is too low, then it is not possible to prepare a stable gel. If, however, the amount of component (b) is set too high, a non-dry formulation of the gel results.

For the purposes of the present invention, some of the polyoxyalkylene-organopolysiloxanes of the general formula (I) can be replaced by the α,ω-polyetherpolysiloxanes of the formula II

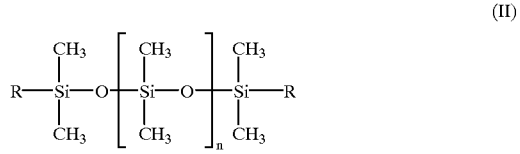

(II)

where
R=—(CH$_2$—)$_m$O—(C$_2$H$_4$O—)$_x$(C$_3$H$_6$O—)$_y$R$^1$
m=2 to 4,
x—3 to 100,
y=0 to 50,
R$^1$=H or alkyl,
n=50 to 200,
and/or polyoxyalkylene-organosiloxanes of the formula (III):

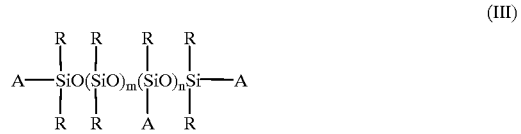

(III)

where
R is alkyl or aryl group,
A is chosen from the group consisting of alkyl, aryl or poloxyalkylene groups of the formula —C$_3$H$_6$O(C$_2$H$_4$O)$_a$(C$_3$H$_6$O)$_b$R',
where R' is chosen from the group consisting of hydrogen, an acyl group or an alkyl group having from 1 to 4 carbon atoms,
a is an integer in the range from 5 to 50,
b is an integer in the range from 5 to 50,
m is an integer in the range from 50 to 1000 and
n is an integer in the range from 1 to 40.

Especially preferred are α,ω-polyetherpolysiloxanes of formula (II) where R$^1$ is H, CH$_3$ or Ch$_2$CH$_3$. Especially preferred α,ω-polyetherpolysiloxanes of formula (III) are those where R is a methyl or a phenyl group and A is a methyl, phenyl or poloyalkylene group of the formula —C$_3$H$_6$O(C$_2$H$_4$O)$_a$(C$_3$H$_6$O)$_b$R$^1$. These polyetherpolysiloxanes are described in the art, e.g. from EP 0 819 426 A2. In this respect, reference is made to the entire disclosure of that laid-open specification For the purposes of the present invention, particular preference is given to replacing from about 10 to about 50% by weight, based on component (b), of the polyoxyalkylene-organopolysiloxane of the formula (I) by the α,ω-polyethersiloxane of the formula (II).

The novel gels preferably comprise from about 10 to about 80% by weight, based on the composition, of water. To adjust the refractive index, alcohols and/or polyols are added to the aqueous phase. For the purposes of the present invention, particular preference is given to the presence of at least about 5% by weight and at most about 78% by weight based on the composition, or at least about 6% by weight and up to about 90% by weight of the aqueous phase, of alcohol and/or polyol. Examples of these compounds include ethanol, n-propanol, isopropanol, primary, secondary and tertiary aliphatic alcohols having at least one and at most six hydroxyl groups and a chain length of from 2 to 6 carbon atoms (ethylene glycol, glycerol, propylene glycol to hexylene glycol. polypropylene glycol, sorbitol and other sugar alcohols), polyglycerols having a degree of condensation of from 2 to 10 (diglycerol, triglycerol . . . ) and mixtures of the polyglycerols with one another and with glycerols.

Where UV absorbers are used in the oil phase in a total amount greater than about 1%, based on the composition, alcohols and/or polyols are needed to adjust the refractive index of the hydrophilic (aqueous) phase. Using water alone, the refractive index does not in most cases reach the corresponding value of the oil phase. Surprisingly, it has been found that these transparent emulsions comprising polyol, water, silicone and polar UV absorbers have thermal and long-term stability, since emulsions with mixed-polarity oil phase and a high polyol content are usually difficult to stabilize.

For the purposes of the present invention, the transparent sunscreen gels particularly preferably comprise UV absorbers chosen from 4-aminobenzoic acid, 3-(4'-trimethylammonium)benzylidenebornan-2-one methyl sulfate, 3,3,5-trimethylcyclohexyl salicylate, 2-hydroxy-4-methoxybenzophenone, 2-phenylbenzimidazol-5-sulfonic acid and its potassium, sodium and triethanolamine salts, 3,3'-(1,4-phenylenedimethine)-bis-(7,7-dimethyl-2-oxobicyclo[2.2.1]heptane-1-methanesulfonic acid) and its salts, 1-(4-tert-butylphenyl)-3-(4-methoxyphenyl)propane-1,3-dione, 3-(4'-sulfo)benzylidenebornan-2-one and salts, 2-ethylhexyl 2-cyano-3,3-diphenylacrylate, polyethoxyethyl 4-bis(polyethoxy)aminobenzoate, 2-ethylhexyl dimethylaminobenzoate, 2-ethylhexyl salicylate, isoamyl 4-methoxycinnamate, 2-ethylhexyl 4-methoxycinnamate, 2-hydroxy-4-methoxybenzophenone-5-sulfonic acid and the sodium salt 3-(4'-methylbenzylidene)bornan-2-one, 3-benzylidenebornane-2-one, 4-isopropylbenzyl salicylate, 2,4,6-trianilino-(p-carbo-2'-ethylhexyl-1'-oxy)-1,3,5-triazine, 3-imidazol-4-yl-acrylic acid and its ethyl ester, and N-([2 and 4]-[(2-oxoborn-3-ylidene)methyl]benzyl) acrylamide polymer or mixtures thereof.

The amount of water-soluble UV absorbers which may be present in the novel transparent sunscreen gels should preferably be from about 1 to about 10% by weight, based on the composition, in particular from about 2 to about 8% by weight, based on the composition.

As well as or instead of the water-soluble UV absorbers, it is, of course, also possible for the purposes of the present invention to use oil-soluble UV absorbers.

The amount of oil-soluble absorbers depends in particular also on the refractive index of this component since, for the preparation of the novel transparent sunscreen gels, the aqueous phase and the silicone oil phase should have the same refractive index. The amount of soluble UV absorbers is preferably from about 1 to about 10% by weight, in particular from about 2 to about 8% by weight, based on the composition.

The silicone gel compositions of the present invention are prepared as in the prior art, in particular EP 0 568 102 A1, by mixing together water, which comprises the UV absorber in solution, into components (a) and (b). The content of water in the silicone gel composition of the present invention is preferably in the range from about 0.2 to about 80% by weight and in particular in the range from about 0.3 to about 75% by weight. A stable gel composition cannot be obtained if the water content is too low. If the water content is set too high, the silicone gel composition separates, and preparation of a stable silicone gel becomes extremely difficult.

WORKING EXAMPLES

The ingredients of (A) and (B) given below were mixed together one at a time in the order given with stirring. With uniform stirring at room temperature, (B) was slowly added to (A). The mixture was then homogenized. For clear formulations, the refractive indices of (A) and (B) must be identical. This can be achieved by slightly changing the water/glycerol ratio. The amounts in % by weight refer in each case to the total amount.

EXAMPLE 1
The formulation was tested for 3 months at 45° C., 2½ months at 60° C. and 5 times at -25° C./room temperature and in all cases did not display separation phenomena.

A:

| | |
|---|---|
| Cetyl dimethicone copolyol (ABIL ®EM 90) | (2% by wt.), |
| Cetyl dimethicone (ABIL ®Wax 9801) | (2% by wt.), |
| Cyclopentasiloxane and cyclohexasiloxane (ABIL ®B8839) | (6.5% by wt.), |
| Isopropyl myristate (TEGOSOFT ®M) | (1% by wt.), |
| Octyldimethyl PABA (Eusolex ®6007 Merck) | (0.5% by wt.), |
| Octyl methoxycinnamate (Parsol ®MCX GIVAUDAN) | (4% by wt.), |

B:

| | |
|---|---|
| Deionized water | (10% by wt.), |
| Sodium chloride | (2% by wt.), |
| Glycerol | (72% by wt.). |

This gave a stable gel with a sun protection factor SPF in accordance with Colipa of 11.

EXAMPLE 2

A:

| | |
|---|---|
| Cetyl dimethicone copolyol (ABIL ®EM 90) | (2% by wt.), |
| Cetyl dimethicone (ABIL ®Wax 9801) | (2% by wt.), |
| Cyclopentasiloxane and cyclohexasiloxane (ABIL ®B8839) | (6.5% by wt.), |
| Isopropyl myristate (TEGOSOFT ®M) | (1% by wt.), |
| Octyldimethyl PABA (Eusolex ®6007 Merck) | (0.5% by wt.), |
| Octyl methoxycinnamate (Parsol ®MCX GIVAUDAN) | (4% by wt.), |
| Butyl methoxydibenzoylmethane | (0.5% by wt.) |

B:

| | |
|---|---|
| Deionized water | (20.95% by wt.), |
| Sodium chloride | (2% by wt.), |
| Glycerol | (53% by wt.) |
| Phenylbenzimidazolesulfonic acid (Neo-Heliopan ® Hydro (Haarmann & Reimer) | (7.8% by wt.) |

EXAMPLE 2 -continued

| | |
|---|---|
| Sodium hydroxide | (0.25% by wt.) | were used to prepare a corresponding gel as in Example 1.

The sun protection factor of the stable gel, determined in vivo (Colipa), was 16.

EXAMPLE 3
Using an exclusively water-soluble filter, a gel was prepared:

A:

| | |
|---|---|
| Cetyl dimethicone copolyol (ABIL ®EM 90) | (2% by wt.), |
| Cetyl dimethicone (ABIL ®Wax 9801) | (2% by wt.), |
| Cyclopentasiloxane and cyclohexasiloxane (ABIL ®B8839) | (11% by wt.), |
| Isopropyl myristate (TEGOSOFT ®M) | (1% by wt.), |

B:

| | |
|---|---|
| Deionized water | (27.75% by wt.), |
| Sodium chloride | (2% by wt.), |
| Glycerol | (27% by wt.), |
| Phenylbenzimidazolesulfonic acid and NaOH as remainder. | (27% by wt.). |

As in the previous examples, here too a stable gel was obtained and the sun protection factor, determined in vivo (Colipa), was 18.

The abovementioned products can be referred to as water-resistant.

The above description of the invention is intended to be illustrative and not limiting. Various changes or modifications in the embodiments described may occur to those skilled in the art. These changes can be made without departing from the spirit or scope of the invention.

Patent claims:

1. A transparent sunscreen gel comprising
   (a) silicone oil
   (b) polyoxyalkylene-organopolysiloxanes of the formula (I)

$$H_3C-SiO\left[\begin{array}{c}CH_3\\|\\SiO\\|\\CH_3\end{array}\right]\left[\begin{array}{c}CH_3\\|\\SiO\\|\\CH_3\end{array}\right]_n\left[\begin{array}{c}CH_3\\|\\SiO\\|\\(CH_2)_3\\|\\O(C_2H_4O)_x(C_3H_6O)_yR\end{array}\right]_m\left[\begin{array}{c}CH_3\\|\\SiO\\|\\(CH_2)_p\\|\\CH_3\end{array}\right]_o\begin{array}{c}CH_3\\|\\Si-CH_3\\|\\CH_3\end{array} \quad (I)$$

where
R is an alkyl radical carbon atoms or a hydrogen radical,
$n=10$ to $200$,
$m=1$ to 25 and
$o=1$ to 100 with the proviso that, in the average molecule, $o \geq m$ and $3o < n$,
$p=7$ to 17, and
the molar mass of the residue $(C_2H_4O-)_x-(C_3H_6O-)_yR$ is from about 250 to about 2000, where x and y are chosen such that the weight ratio of oxyethylene groups to oxypropylene groups is from 100:0 to about 20:80,
   (c) water,
   (d) a component chosen from alcohols and/or polyols and
   (e) at least one UV absorber which is soluble in the aqueous or in the oily phase.

2. The gel as claimed in claim 1, wherein R is an alkyl radical having from 1 to 4 carbon atoms or a hydrogen radical and the molar mass of the residue $(C_2H_4O\!-\!)_x\!-\!(C_3H_6O)_yR$ is from 250 to 2000, where x and y are chosen such that the weight ratio of oxyethylene groups to oxypropylene groups is from 100:0 to 20:80.

3. The gel as claimed in claim 1, wherein the silicone oil (a) is selected from the group consisting of polysiloxane-polyalkylene copolymers, low-viscosity to high-viscosity diorganopolysiloxanes, cyclic siloxanes; solutions of cyclic siloxanes having a high molar mass; solutions of dimethylpolysiloxane gums, dimethylsiloxanemethylphenylsiloxane copolymer gums and dimethylpolysiloxane gums; trimethylsiloxysilicic acids and cyclic siloxane solutions of trimethylsiloxysilicic acids; diorganopolysiloxanes having $C_6$ to $C_{50}$ alkyl groups; and diorganopolysiloxanes containing amino groups.

4. The gel as claimed in claim 3, wherein the silicone oil (a) is dimethylpolysiloxanes, methylphenylpolysiloxanes and siloxane-methylphenylsiloxane copolymers.

5. The gel as claimed in claim 1 wherein the silicone oil (a) is present in an amount of from about 10 to about 80% by weight.

6. The gel as claimed in claim 1, wherein the polyoxyalkylene-organopolysiloxanes of formula (I) are present in an amount of from about 2 to about 30% by weight, based on the overall composition.

7. The gel as claimed in claim 6, wherein the polyoxalkylene-organopolysiloxanes of formula (I) are present in an amount of from about 5 to about 15% by weight, based on the overall composition.

8. The gel as claimed in claim 1, wherein the component (b) further comprises α,ω-polyetherpolysiloxanes of the formula (II)

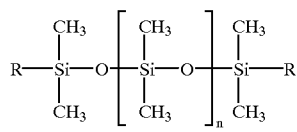

(II)

where
$R=\!\!-\!(CH_2\!-\!)_mO\!-\!(C_2H_4O\!-\!)_x(C_3H_6O\!-\!)_yR^1$
m=2 to 4,
x=3 to 100,
y=0 to 50,
$R^1$=H or alkyl,
n=50 to 200,
and/or polyoxyalkylene-organosiloxanes of the formula (III):

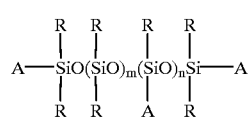

(III)

where
R is an alkyl or an aryl group,
A is chosen from the group consisting of alkyl, aryl or poloxyalkylene groups of the formula $-\!C_3H_6O(C_2H_4O)_a(C_3H_6O)_bR'$,
where R' is chosen from the group consisting of hydrogen, an acyl group or an alkyl group,
a is an integer in the range from 5 to 50,
b is an integer in the range from 5 to 50,
m is an integer in the range from 50 to 5000 and
n is an integer in the range from 1 to 40.

9. The gel as claimed in claim 1, wherein the component (b) comprises α,ω-polyetherpolysiloxanes of the formula (II)

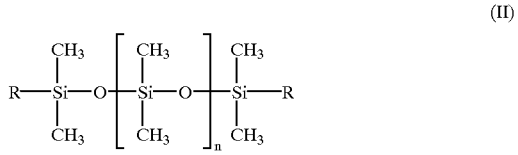

(II)

where
$R=\!\!-\!(CH_2\!-\!)_mO\!-\!(C_2H_4O\!-\!)_x(C_3H_6O\!-\!)_yR^1$
m=2 to 4,
x=3 to 100,
y=0 to 50,
$R^1$=H, $CH_3$, $CH_2CH_3$,
n=50 to 200,
and/or polyoxyalkylene-organosiloxanes of the formula (III):

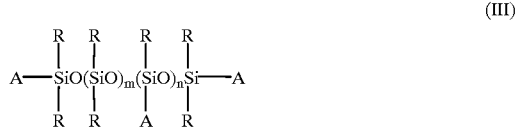

(III)

where
R is a methyl or phenyl group,
A is chosen from the group consisting of methyl, phenyl or poloxyalkylene groups of the formula $-\!C_3H_6O(C_2H_4O)_a(C_3H_6O)_bR'$,
where R' is chosen from the group consisting of hydrogen, an acyl group or an alkyl group having from 1 to 4 carbon atoms,
a is an integer in the range from 5 to 50,
b is an integer in the range from 5 to 50,
m is an integer in the range from 50 to 1000 and
n is an integer in the range from 1 to 40.

10. The gel as claimed in claim 8, wherein the α,ω-polyether-siloxanes of the formula (II) and/or polyoxyalkylene-organopolysiloxane of the formula (III) is present in an amount of from about 10 to about 50% by weight, based on component (b).

11. The gel as claimed in claim 1, wherein the water content is from about 10 to about 80% by weight, based on the overall composition.

12. The gel as claimed in claim 1, wherein the content of alcohols and/or polyols in component (d) is from about 5 to about 78% by weight based on the overall composition.

13. The gel as claimed in claim 1, wherein the content of alcohols and/or polyols in component (d) is from about 6 to about 90% by weight based on the aqueous phase.

14. The gel as claimed in claim 1, wherein the alcohols and polyols are primary, secondary and tertiary aliphatic alcohols having at least one and at most six hydroxyl groups and a chain length of from 2 to 6 carbon atoms, and polyglycerols having a degree of condensation of from 2 to 10, and mixtures of the polyglycerol with one another and with glycerols.

15. The gel as claimed in claim 14, wherein the alcohols and polyols are selected from the group consisting of ethanol, n-propanol, isopropanol, ethylene glycol, glycerol, propylene glycol, hexylene glycol, sorbitol, diglycerol and triglycerol.

16. The gel as claimed in claim 1, wherein the UV absorbers are selected from the group consisting of 4-aminobenzoic acid, 3-(4'-trimethylammonium) benzylidenebornan-2-one methyl sulfate, 3,3,5-trimethylcyclohexyl salicylate, 2-hydroxy4-methoxybenzophenone, 2-phenylbenzimidazol-5-sulfonic acid and its potassium, sodium and triethanolamine salts, 3,3'-(1,4-phenylenedimethine)-bis-(7,7-dimethyl-2-oxobicyclo[2.2.1]heptane-1-methanesulfonic acid) and its salts, 1-(4-tert-butylphenyl)-3-(4-methoxyphenyl)propane-1,3-dione, 3-(4'-sulfo)benzylidenebornan-2-one and salts, 2-ethylhexyl 2-cyano-3,3-diphenylacrylate, polyethoxyethyl 4-bis(polyethoxy)-aminobenzoate, 2-ethylhexyl dimethylaminobenzoate, 2-ethylhexyl salicylate, isoamyl 4-methoxycinnamate, 2-ethylhexyl 4-methoxycinnamate, 2-hydroxy4-methoxybenzophenone-5-sulfonic acid and the sodium salt, 3-(4'-methylbenzylidene)bornan-2-one, 3-benzylidenebornane-2-one, 4-isopropylbenzyl salicylate, 2,4,6-trianilino-(p-carbo-2'-ethylhexyl-1'-oxy)-1,3,5-triazine, 3-imidazol-4yl-acrylic acid and its ethyl ester, and N-([2 and 4]-[(2-oxoborn-3-ylidene)-methyl]benzyl) acrylamide polymer or mixtures thereof.

17. The gel as claimed in claim 1, wherein the amount of water-soluble UV absorbers is from about 1 to about 10% by weight, based on the overall composition.

18. The gel as claimed in claim 1, wherein the amount of oil-soluble UV absorbers is from about 1 to about 10% by weight, based on the overall composition.

* * * * *